United States Patent [19]

Friedman et al.

[11] Patent Number: 5,290,169
[45] Date of Patent: Mar. 1, 1994

[54] OPTICAL LIGHT GUIDE FOR DENTAL LIGHT-CURING LAMPS

[76] Inventors: Joshua Friedman, 11 Boulevard Dr. Unit 2, Danbury, Conn. 06810; Brian Dell, P.O. Box 2635, Waterbury, Conn. 06702

[21] Appl. No.: 970,038
[22] Filed: Nov. 2, 1992
[51] Int. Cl.⁵ ............................ A61C 1/00; A61C 3/00
[52] U.S. Cl. ............................................ 433/29; 433/229
[58] Field of Search ........................... 433/29, 229, 215; 128/397, 398; 385/83, 147, 902

[56] References Cited

U.S. PATENT DOCUMENTS

| | | | |
|---|---|---|---|
| 1,542,183 | 6/1923 | Steinberg . | |
| 2,186,143 | 1/1940 | Neugass | 128/398 |
| 3,712,984 | 3/1971 | Lienhard | 128/397 |
| 4,666,406 | 5/1987 | Kanka, III | 433/229 |
| 4,792,692 | 12/1988 | Herold et al. | 385/902 |
| 4,836,782 | 6/1989 | Gonser | 433/229 |
| 4,948,215 | 8/1990 | Friedman | 350/96.10 |

FOREIGN PATENT DOCUMENTS 2901534  7/1979  Fed. Rep. of Germany ...... 433/229

Primary Examiner—Gene Mancene
Assistant Examiner—Cindy A. Cherichetti
Attorney, Agent, or Firm—E. Lieberstein

[57] ABSTRACT

The optical light guide of the present invention is composed of a solid, transparent material selected from the class consisting of glass, acrylic, polystyrene, and polycarbonate. The light guide has a head, a tapered section and a curved section. The head has a light-receiving, concave surface geometry at the proximal end of the light guide.

11 Claims, 5 Drawing Sheets

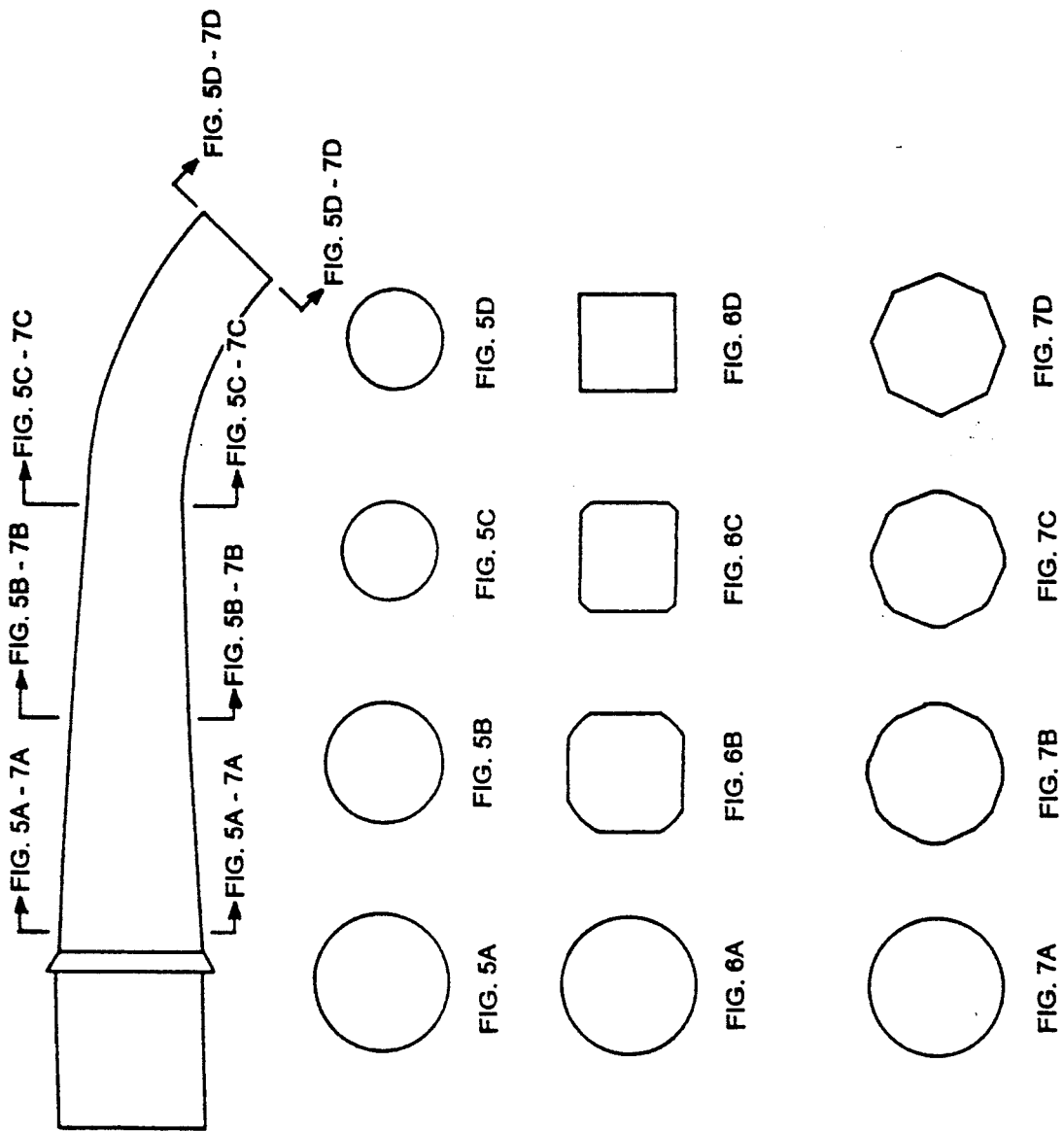

OPTICAL LIGHT GUIDE FOR DENTAL LIGHT-CURING LAMPS

FIELD OF THE INVENTION

This invention relates to an optical light guide for directing radiant energy from a source of light to the treatment site of a light-curable dental restoration.

BACKGROUND OF THE INVENTION

The use of photocurable dental materials in the practice of restorative dentistry has become popular. Photocurable materials are cured by exposure to radiant energy in a preselected spectral range, typically in either the long-wave ultraviolet or blue visible spectrum, tailored to the composition of the photocurable material to be cured. A light-curing unit containing a reflector lamp is used to irradiate the photocurable material by directing light from the reflector lamp through a light guide, with its distal end positioned contiguous to the photocurable material to be cured. The light guide functions to channel the light to the material at the site of a dental restoration, and should lose as little light as possible to the surrounding environment. However, to assure maximum maneuverability of the light guide within the oral cavity, it is desirable for the light guide to be curved at its distal end through an angle which should lie between thirty (30°) and ninety degrees (90°), although an angle of between thirty (30°) and sixty degrees (60') is preferred. To satisfy the curved geometry requirement without suffering a substantial loss in light transmission, particularly through the curved section, it is, at present, conventional to construct the light guide from a fiber-optic conductor. Generally, a fiber-optic conductor consists of either multiple glass fiber strands held together in the form of a "flexible bundle," or fused into a solid rod of individual fibers. The use of multiple glass fiber strands, each small in diameter, permits the fiber-optic rod to be curved with little loss in light transmission. However, the fiber-optic bundle and the fused fiber-optic rod are relatively expensive to manufacture. Moreover, the solid, fused fiber-optic rod, although more desirable, is fragile, and, if dropped, will readily fracture or break.

A solid, optical conductor composed of a transparent, solid, unitary glass or plastic rod having a curved geometry would have significant economic and practical advantages over the conventional fiber-optic rod, provided light could be transmitted through the rod without suffering significant loss in light transmission. Several alternatives to the fiber-optic light guide have been proposed in the prior art such as using a hollow, transmitting, cone-shaped light collector with internal reflecting mirrors, a higher powered light source, or simply ignoring the preference of the dental profession for a contoured light guide with a large angle of curvature at the distal end. These alternatives have not proven to be practical or desirable.

SUMMARY OF THE INVENTION

An optical light guide composed of a solid, transparent material selected from the class consisting of glass, acrylic, polystyrene, or polycarbonate has been developed, in accordance with the present invention, having a curved configuration, with an angle of curvature greater than thirty degrees (30°), without suffering substantial loss in light transmission. In fact, light is transmitted with an efficiency of transmission essentially equal to that obtained from the conventional fiber-optic light guide. However, the optical light guide of the present invention is substantially lighter in weight compared to the conventional fiber-optic rod, is resistant to breakage, can be disposed of readily, and is substantially less expensive to manufacture.

The optical light guide of the present invention comprises a solid, unitary rod, composed of a material selected from the class consisting of glass, acrylic, polystyrene, and polycarbonate, with said solid rod having a head, means for intercoupling the head to a source of light along the optic axis of the light source, a tapered section extending from said head, a curved section extending from said tapered section, with said curved section having an angle of curvature of between thirty (30°) and sixty degrees (60°) relative to the longitudinal axis of said tapered section, and with said rod having a light receiving surface at the proximal end of said light guide for receiving incident light projected from said light source. The curved section may terminate at the distal end of the light guide or may represent an intermediate section, with the optical light guide having another straight section extending from the curved section, and terminating at the distal end of the light guide.

BRIEF DESCRIPTION OF THE DRAWINGS

Other objects and advantages of the present invention will become apparent from the following detailed description of the invention, when read in conjunction with the accompanying drawings, of which:

FIG. 5 is another view, similar to FIG. 4, identifying the cross-sections for FIGS. 5A–5D, FIGS. 6A–6D, and FIGS. 7A–7D, respectively;

FIGS. 5A–5D are cross-sections taken along the lines A—A, B—B, C—C, and D—D of FIG. 5;

FIGS. 6A–6D are alternative cross-sections taken along the lines A—A, B—B, C—C, and D—D of FIG. 5; and FIGS. 7A–7D are yet other alternative cross-sections taken along the lines A—A, B—B, C—C, and D—D of FIG. 5.

DETAILED DESCRIPTION OF A PREFERRED EMBODIMENT OF THE PRESENT INVENTION

Figure 1:
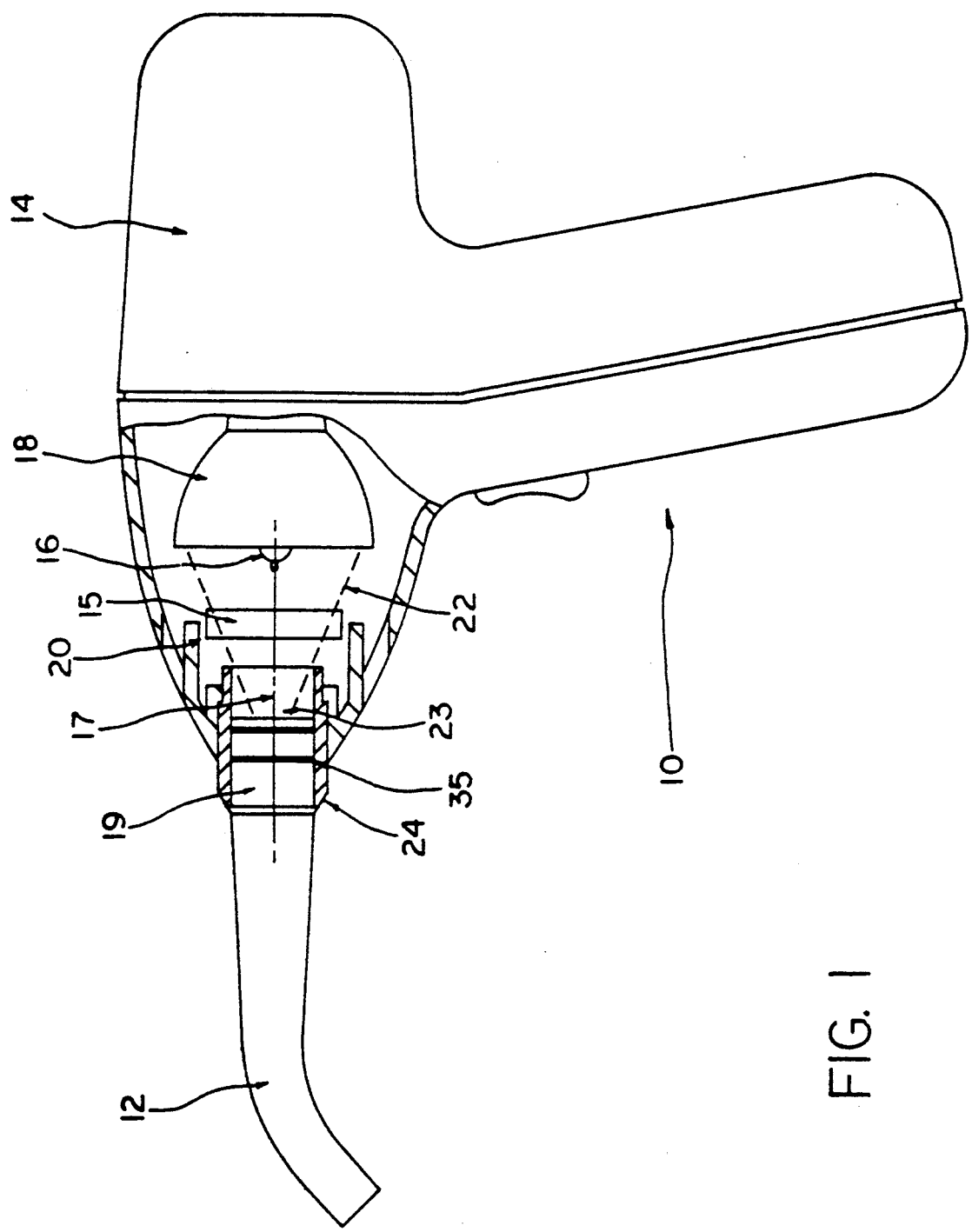
FIG. 1 is a longitudinal view, partially in section, of a conventional hand held light gun in combination with the optical light guide of the present invention.
Figure 2:
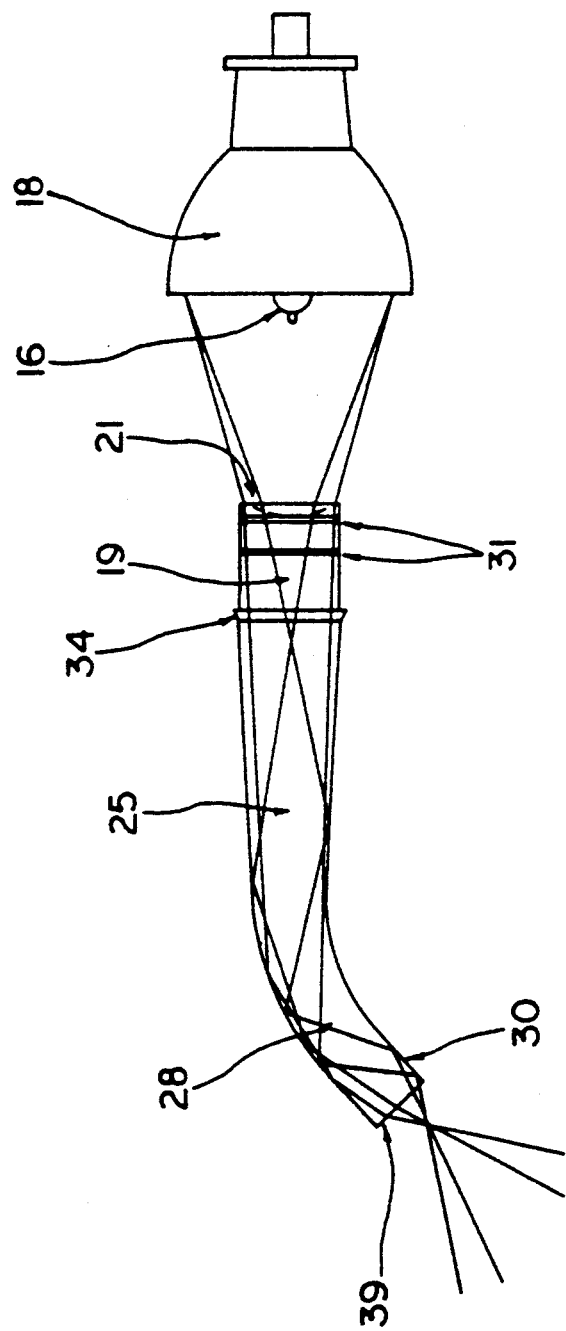
FIG. 2 is an exploded longitudinal view of the light guide of the present invention shown in schematic relationship to a source of light, and to a restorative site which is to be exposed to light energy through said light guide.

A hand held dental light-curing gun (10) is shown in FIGS. 1 and 2, in combination with the light guide (12) of the present invention. The hand held dental light gun (10) includes a housing (14) containing a source of radiant energy, such as a halogen lamp (16), a reflector (18) surrounding the halogen lamp (16), and a suitable filter or filter assembly (15). The lamp (16) may be of the tungsten/halogen type, or of the mercury vapor, short arc xenon, or metal-halide type, dependent on the desired spectral bandwidth of radiant energy. The filter assembly (15) is affixed to a bracket (20) connected to the housing (14) which holds the filter assembly (15) a predetermined distance from the lamp (16) along the optic axis (17) for filtering out unwanted radiant energy. The reflector (18) has an elliptical shape for reflecting and focusing light energy through the filter assembly (15) to the light guide (12). For a typical sized halogen lamp (16), the focused light energy beam (22) converges to a focal spot (23), which is contiguous to the proximal end (21) of the light guide (12). The light guide (12) is mounted in a bushing (24) affixed to the housing (14).

The light guide (12) has a head (19) adapted to be inserted into the bushing (24) of the light gun (10), an intermediate straight section (25) of a predetermined, relatively short length, and a curved section (28) extending from an intermediate section (25). The section (25) has a nominal convergent taper, as will hereafter be further described. Another straight section (30) may optionally be added to the curved section at the distal end of the light guide. The head (19) is cylindrical in geometry and has at least one circular groove (31) surrounding its periphery, and a chamfered flange (34) spaced a predetermined distance from the groove (31). The flange (34) is flush-mounted against the light gun (10) upon insertion of the head (19) into the bushing (24). The bushing (24) has a complementary circular groove (35) with a split ring (not shown) which snaps over the groove (31) to firmly hold the head (19) within the light gun (10) in a position concentric to the optic axis (17), and with the proximal end (21) of the light guide (12) substantially contiguous to the focal spot (23) of the light energy beam (22).

Figure 3:
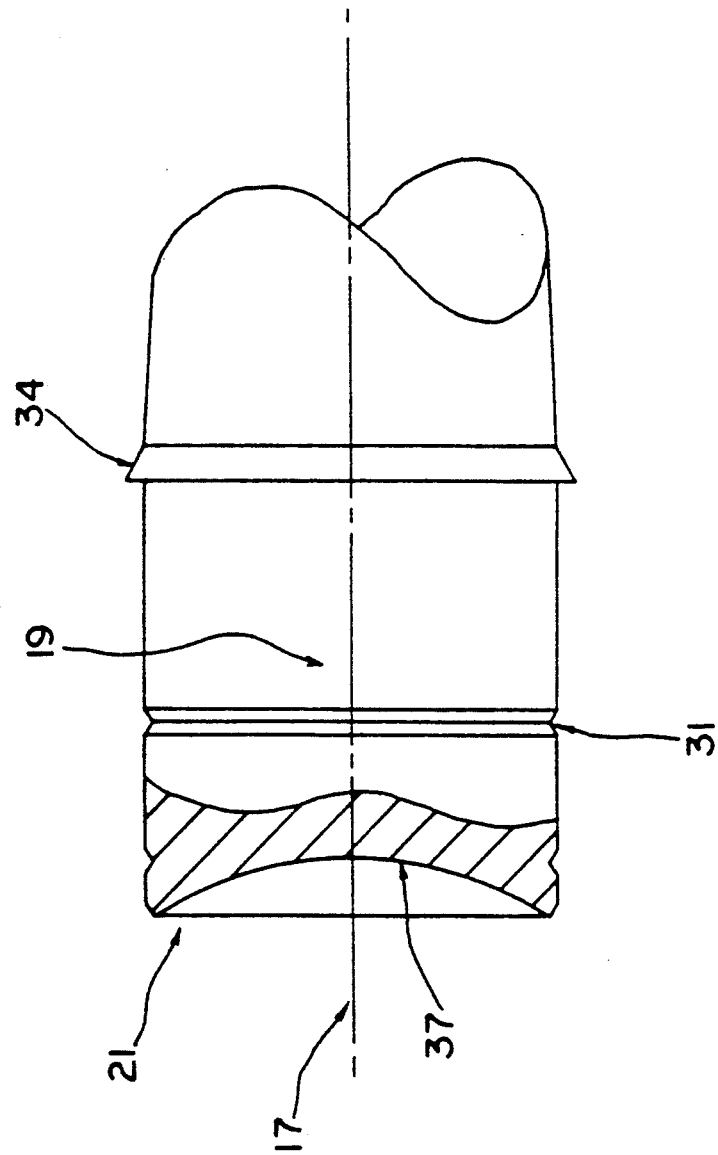
FIG. 3 is a view in cross-section of the head of the light guide of FIG. 2.

The proximal end (21) of the light guide (12) has a hemispherical geometry which forms a concave, light-receiving surface (37) with a relatively deep concavity, as shown in FIG. 3, with the center of the concavity on the optic axis (17). The light-receiving surface (37) minimizes the angle of internal refraction to incident light striking the surface (37), so that the direction of the light rays internal of the light guide (12) is collimated in a direction relatively parallel to the optic axis (17). The optic axis (17) is coincident with the longitudinal axis of the straight section (25) of the light guide (12). The light-receiving surface (37) reduces the number of internal reflections of light within the light guide (12), as a result of extending the linear distance of internally refracted light from the light-receiving surface (37) to the boundary interface between the light guide (12) and air. Thus, the number of internal reflections is minimized. This should be clearly apparent from the light rays shown traversing the optical light guide in FIG. 2.

The intermediate section (25) is tapered, starting from the flange (34), with a nominal, convergent taper of between one to five degrees (10°-50°) relative to the longitudinal axis, and preferably between 2.5 and 3.5 degrees. The taper reduces the angle of incidence which results in the concentration of the light rays at the distal end. However, with each reflection of light within the tapered section, the angle of incidence decreases by an amount equal to twice the taper angle until it is smaller than the critical angle, at which point light escapes from the light guide (12) in accordance with Snell's law of refraction. The critical angle is defined as that angle of incidence which results in light being refracted out of the light guide into the air and at an angle of refraction equal to ninety (90°) degrees. Accordingly, as long as the tapered angle is confined to a small angle, to avoid loss in light, the taper will help concentrate the light, yielding an increase in power density.

The curved section (28) has a radius of curvature which is chosen in proportion to the diameter of the light guide (12), and to provide the degree of maneuverability needed to access any tooth surface in the oral cavity. An angle of curvature of from thirty degrees (30°) to sixty degrees (60°) is preferred for a chosen diameter of between 0.3 to 0.6 inches. The curved section (28) uniformly distributes the light exiting the light guide (12), and preferably tapers in cross-section show that the cross-section at its distal end is smaller than the cross-section of section (25). An optional straight section (30) may be added to the end of the curved section (28) to form the distal end (39) of the light guide. The straight section (30) may, if desired, also be tapered and may be of any desired cross-section. In use, the light guide (12) is placed in very close proximity to the tooth surface to be restored.

The light guide (12) is composed of a solid, transparent material, preferably selected from the class consisting of glass, acrylic, polystyrene, and polycarbonate and having a refractive index preferably above 1.4. A solid light guide of acrylic is preferred.

Figure 4:
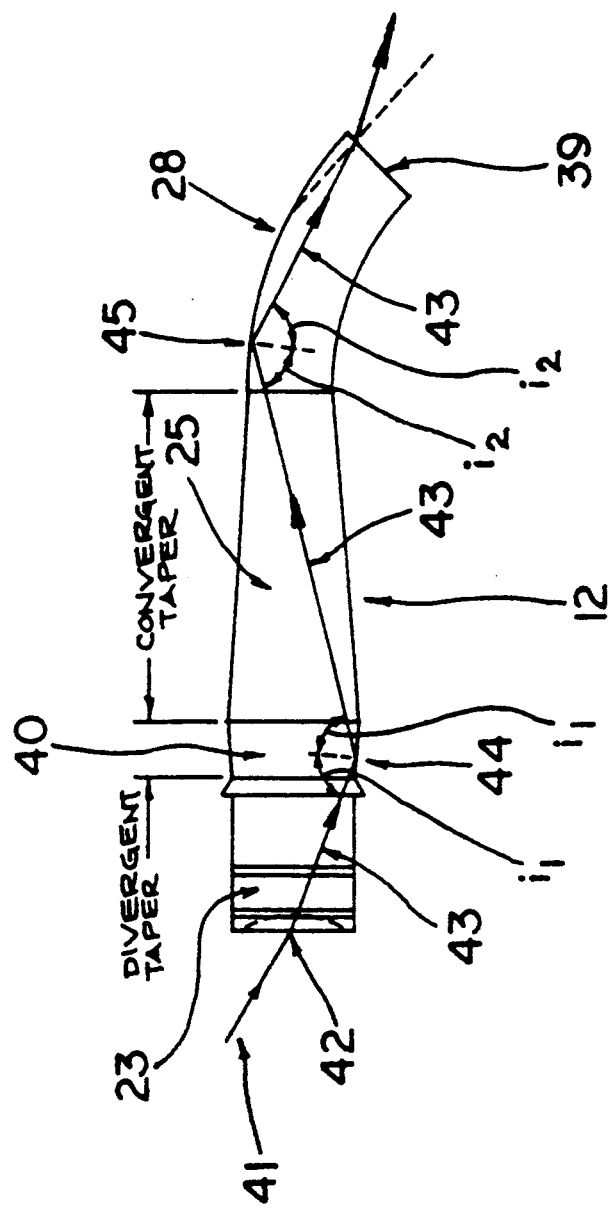
FIG. 4 is a longitudinal view of an alternate embodiment of the optical light guide of the present invention.

An alternate embodiment of the light guide (12) is shown in FIG. 4. The principal difference between this embodiment and the configuration shown in FIG. 2 is the addition of a divergent section (40) between the head (19) and the converging, tapered section (25). An example incident light ray (41) is shown refracted at (42) into the light guide (1 2) where it continues as an internal light ray (43), striking the first internal reflection point (44) within the divergent, tapered section (40) at an angle of incidence ($i_1$). The internal light ray (43) is then reflected to the next internal reflection point (45), which lies within the curved section (28) at an angle of incidence ($i_2$), from which the light ray (43) is again reflected (45) to the exit face (39) of the light guide (12), and is then refracted into the air so as to strike the site of the restoration. If the divergent section (40) is not included, then certain light rays with large incident angles at the point of refraction (42) into the light guide (12) may escape out of the light guide (1 2) before reaching the exit face (39). Thus, the addition of a divergent, tapered section (40) will be useful in certain cases in which extreme angle rays are reflected from the light reflector (18) in the light gun (10).

Other alternate embodiments which may be used in conjunction with, or independent of, the embodiment of FIG. 4 is shown FIGS. 5, 6, and 7. In the embodiment of FIG. 5, the converging section (25) is nonuniform in cross-section, and may have a plurality of different cross-sections, such as is shown in FIGS. 5A-5D, FIGS. 6A-6D, or FIGS. 7A-7D, at different positions along its length. The purpose of the plurality of different cross-sections is to control the uniformity of luminance exiting the light guide (12). This may be desirable when the incident light on the proximal surface (37) of the light guide is nonuniform in intensity. Any such nonuniformity will be transmitted to the output end face (39), which may result in an unsatisfactory cure of the photocurable material. In the embodiment of FIGS. 5, 6, and 7, the tapered section (25) is initially circular in cross-section, and then gradually merges into a polygonal or square cross-section at the distal end. The multiple, radially random reflections from the flat surfaces of the polygon effectively destroy any intensity structure in the total beam, resulting in an output uniform in radiometric intensity.

What we claim is:

1. An optical light guide for transmitting light from a light source to a dental restorative site to cure a photocurable material, comprising a solid, unitary rod composed of a rigid, transparent material, optically coupled at the proximal end thereof to said light source through an optical surface of hemispherical geometry, with said rod including a tapered section, a curved section extending from said tapered section, and a tapered section, a curved section extenting thereof.

2. An optical light guide, as defined in claim 1, wherein said curved section has an angle of curvature of between thirty (30°) and sixty degrees (60°) relative to the longitudinal axis of said tapered section.

3. An optical light guide, as defined in claim 2, wherein said rod is composed of an acrylic resin.

4. An optical light guide, as defined in claim 3, wherein said tapered section has a converging, tapered angle of between two (2°) to five (5°) degrees.

5. An optical light guide, as defined in claim 4, wherein said tapered angle is between 2.5 and 3.5 degrees.

6. An optical light guide, as defined in claim 4, wherein said tapered section includes a diverging portion disposed between said head and said converging section.

7. An optical light guide, as defined in claim 2, further comprising an additional straight section extending from said curved section.

8. An optical light guide, as defined in claim 7, wherein said additional straight section is uniform in cross-section.

9. An optical light guide, as defined in claim 7, wherein said additional straight section is nonuniform in cross-section.

10. An optical light guide, as defined in claim 9, wherein said additional straight section has a plurality of cross-sectional shapes, including a polygon.

11. An optical light guide, as defined in claim 2, wherein said means for intercoupling said head to said source of light comprises at least one circular groove and a chamfered flange spaced from said circular groove.

* * * * *